United States Patent [19]

Jackson et al.

[11] 4,031,198

[45] June 21, 1977

[54] TECHNETIUM-LABELED COMPLEXES, PRODUCTION AND USE THEREOF

[75] Inventors: Richard A. Jackson, White Bear Lake; Theodore F. Bolles, Woodbury, both of Minn.

[73] Assignee: Minnesota Mining and Manufacturing Company, St. Paul, Minn.

[22] Filed: May 30, 1974

[21] Appl. No.: 474,377

Related U.S. Application Data

[62] Division of Ser. No. 285,079, Aug. 30, 1972, Pat. No. 3,873,680.

[52] U.S. Cl. .................... 424/1; 23/230 B; 23/230.6; 252/301.1 R
[51] Int. Cl.$^2$ .................. G01N 23/00; G21H 5/02
[58] Field of Search ....... 23/230 B, 253 R, 253 TP; 424/1, 9; 252/408, 301.1; 250/303

[56] References Cited

UNITED STATES PATENTS

| | | | |
|---|---|---|---|
| 3,516,794 | 6/1970 | Murty et al. | 23/253 X |
| 3,707,353 | 12/1972 | Kubiatowicz | 23/230 B |
| 3,768,979 | 10/1973 | Mead et al. | 23/230 B |

*Primary Examiner*—R.E. Serwin
*Attorney, Agent, or Firm*—Cruzan Alexander; Donald M. Sell; Carolyn A. Bates

[57] ABSTRACT

A radiopharmaceutical kit for complexing a liver-specific agent labeled with technetium-99m comprising (1) a biologically sterile aqueous medium wherein the complex formation occurs, (2) a complexing agent which is a lipophilic mercaptan or thioketal and (3) a pharmaceutically acceptable reducing agent for technetium-99m.

2 Claims, No Drawings

TECHNETIUM-LABELED COMPLEXES, PRODUCTION AND USE THEREOF

This is a division of application Ser. No. 285,079 filed Aug. 30, 1972, now U.S. Pat. No. 3,873,680.

FIELD OF THE INVENTION

This invention relates to chemical complexes of technetium. An aspect of this invention relates to chemical complexes of the radioactive, metastable isotope technetium-99m (Tc-99m). A further aspect of this invention relates to complexes of technetium-99m wherein the complexing agent is a lipophilic sulfur-containing compound such as a mono- or polymercaptan or a mono- or polythioketal. A further aspect of this invention relates to a process for producing the chemical complex and a preferred biologically sterile substantially isotonic medium containing the complex. Still another aspect of this invention relates to the use of the processes and products of this invention in studies of liver and/or gallbladder function.

DESCRIPTION OF THE PRIOR ART

The art of radiochemistry has found many applications in the fields of medicine and biology. It has long been known that the introduction into an organism of compounds containing (or "labeled" with) a radioisotope can provide insight into the anatomy and physiology of the organism. These compounds, generally referred to as radiopharmaceuticals, are particularly useful in diagnostic techniques which involve studying the structure or function of various internal organs, e.g. the brain, with radiation detection means. For diagnostic work, isotopes with a short half life and an emission spectrum rich in gamma rays (as opposed to beta particles) are preferred.

The metastable isotope Tc-99m has a 6 hour half-life and an emission spectrum, 99% gamma radiation at 140 KeV, which is extremely well suited for techniques of diagnostic nuclear medicine. Thus, Tc-99m has a high specific activity, $5.28 \times 10^9$ millicuries per gram (mc/g), and a conveniently rapid rate of decay; whereas its daughter product, Tc-99, has a specific activity which is almost nine orders of magnitude lower and a half life which is roughly eight orders of magnitude longer. For the organism being studied or diagnosed, the slow rate of decay from the relatively stable, low specific activity Tc-99 to its degradation product (ruthenium) would not normally produce any hazardous amounts of radiation, regardless of the biological means or route of elimination of a Tc-99m radiopharmaceutical. For the researcher or clinician, the emission spectrum of Tc-99m can provide high levels of accuracy in radiodiagnostic measurements and calculations. In recent years, Tc-99m has become readily available in hospitals through the use of selective elution from a so-called molybdenum-99 (Mo-99) generator. The isotope Mo-99 produces Tc-99m as a radioactive decay product.

Although Tc-99m compounds would appear to be ideal radiopharmaceuticals for diagnostic use, providing or selecting Tc compounds or complexes with a view toward organ specificity and tolerable levels of toxicity is a complex task. Obviously, compounds with a very low LD 50 are undesirable for human or veterinary use, even in the small amounts called for by diagnostic work. Compounds with insufficient in vivo stability may be poor diagnostic tools, since radioactive ions or other chemical species with insufficient or undesired organ specificity may be liberated. Stable compounds which become distributed generally throughout the organism, despite their stability, or which do not reach a desired destination in the organism are also poorly suited for many studies of organ function or structure, e.g. liver and gallbladder studies. For these studies of organ function, compounds which are specific to an organ, but which are not excreted by it (or if excreted, are easily reabsorbed) are also poor candidates.

The problem of selecting or preparing a liver specific radiopharmaceutical for liver function studies is particularly difficult. Both the liver and the kidney are capable of removing various types of compounds from the body — ultimately through excretion in feces and urine, respectively. Any radiopharmaceutical used for this purpose should ideally have 100% liver specificity and 0% kidney specificity. Ideally, the compound should also be readily excreted by the liver into the bile. A number of biological and chemical factors must be considered and brought under control before the desired organ specificity and route of excretion can be obtained. For example, some Tc compounds are easily transformed to $TcO_2$, which may lodge in the liver but may not be easily excreted.

Technetium-99m compounds have been used in brain or other organ scanning. For example, Tc-sulfur colloid can be used for liver scanning. Organ scanning is useful for studies of organ structure, but gives little insight into organ function. Representative of the literature relating to the radiopharmacology of Tc-99m compounds are the following articles:

Larson et al., *J. Nuclear Medicine*, 7:8:7 (1966), relating to Tc-99m-colloid preparation for photoscanning, and Tubis et al., *International Journal of Applied Radiation and Isotopes*, V. 19, 835 (1968), relating to Tc-99m labeled cystine, methionine, and a synthetic polypeptide and their distribution in mice.

Compared to the common transition metals, very little is known about the chemistry of technetium. Technetium belongs to Group VII-B of the Periodic Table; its chemistry bears a superficial resemblance to manganese but tends to be more similar to the higher member of the Group, rhenium. Technetium can apparently exist in a range of oxidation states, including +7 (e.g. pertechnetate) and several lower oxidation states, some of which are difficult to characterize and/or are relatively unstable. In spectrophotometric determinations of technetium, the element has been complexed with toluene-3,4-dithiol, thioglycolic acid, and thiocyanates. See Miller et al, *Anal. Chem.*, Page 404 (1961) and Page 1429 (Oct., 1960), and Crouthamel, *Anal. Chem.*, page 1756 (Dec., 1957).

Accordingly, this invention contemplates providing complexes of Tc-99m which have sufficient in vivo stability and a sufficiently high LD 50 for use in humans or animals and which preferably are:

Removed from the blood or other vital organs or tissues by the liver rather than by, for example, the kidneys or the lungs, Concentrated in the liver at a high rate, Concentrated in other organs or tissues — particularly organs or tissues in close proximity to the liver — at a very low or negligible rate, Retained for a short period of time by the liver and secreted into the bile, Removed ultimately from the body by means of a route passing through the gallbladder and intestines to the feces, and Eliminated from the body by alternative routes, (e.g. kidney — bladder — urine) to a minor, preferably negligible, extent.

This invention further contemplates means and methods whereby Tc complexes can be most efficiently produced and utilized for liver function studies.

BRIEF SUMMARY OF THE INVENTION

Briefly, this invention involves reducing an appropriate amount of radioactive pertechnetate ion ($^{99m}TcO_4^-$) until a major amount of the pertechnetate ion has been reduced to a technetium species having an oxidation state greater than 0 but less than +7 and then reacting this technetium species with an excess of one of the subsequently described sulfur-containing complexing agents. The resulting Tc-99m complex is suitable for injection into the blood stream of a mammal when dissolved or dispersed in a biologically sterile aqueous medium substantially isotonic with mammalian body fluids. The reduction step can be carried out chemically through acid catalysis if the complexing agent is also a reducing agent, at least when the complexing agent is present in large excess, as will normally be the case. Preferably, however, reduction is achieved through the use of an additional reducing agent such as a tin (II) salt, an iron (II) salt, a copper (I)/copper (II) couple, or a combination of two or more of these agents.

A meaningful picture of liver function will be obtained by measuring the radioactivity emitted from the liver, gall-bladder, intestines, and feces of the organism or patient being studied. It will generally not be necessary to monitor the radioactivity for more than about 24 hours after the injection, and 12 hours of monitoring can be fully sufficient.

Products produced by the previously described process can have the desired liver specificity if the complexing agent belongs to one of the following four classes of sulfur-containing compounds:

A. A lipophilic compound of the formula

wherein $R^1$ and $R^2$ are the same or different in each repeating unit and can be hydrogen, lower alkyl, or mercapto, n is an integer ranging from 1 to about 6, and X is a mammalian blood-solubilizing polar group which only partially reduces the lipophilic properties of the Tc complex, whereby the complex is readily taken up by the liver in preference to the kidney, despite the X group;

B. A lipophilic compound of the formula

HS—A—X wherein

A is a cycloaliphatic or heterocyclic aliphatic ring, and

X is as defined previously;

C. A lipophilic thioenol or thioketal substituted on the thioketal- or thioenol-carbon with a water solubilizing group and, on the carbon alpha to the thioketal- or thioenol-carbon, with a lipophilic group; and D. A carbocyclic or heterocyclic aromatic carboxylic, sulfonic, or phosphonic acid bearing a mercapto group substituted more remotely than ortho to the carboxylic, sulfonic, or phosphonic acid group.

DETAILED DESCRIPTION OF THE INVENTION

As pointed out previously, complexing agents elected for use in this invention are capable of providing a Tc-99m liver specific compound which is suitable for inclusion in injectable media substantially isotonic with mammalian body fluids, which in vivo is rapidly removed from the blood or other tissues by the liver, is excreted by the liver into the bile, and therefore into the gut (directly or through the gall-bladder), is excreted completely from the gut into the feces, and is not, to any great extent, removed by other organs nor reabsorbed once excreted by the liver. Thus, selection of complexing agents according to this invention involves weighing a combination of chemical and biological criteria. Chemical considerations alone do not insure that the compound will have a liver specificity, compatibility with blood or other mammalian body fluids, or the like. The complexing agent, furthermore, cannot be considered in a vacuum apart from the properties of the complex which will result after reaction with technetium. For example, some complexing agents are lipophilic and are eliminated by the liver, but tend to form stable, insoluble complexes with technetium which would not be secreted into the bile.

Despite all these difficulties of predicting utility of potential complexing agents from chemical criteria alone, it has now been found that partition coefficient data of the Tc complexes provides considerable insight into the proper balance of lipophilic and hydrophilic properties characteristic of a good liver specific complex. These partition coefficient studies involve plotting pH vs. The natural logarithm of the ratio of the activity in water to the activity in normal octyl alcohol, hereinafter referred to as $ln(a_w/a_o)$. In the pH range of 5 to 8, the complex should not be so lipophilic as to have an $ln(a_w/a_o)$ of less than −2, particularly at the higher pH levels. On the other hand, the hydrophilicity must also be kept within limits, as the following table illustrates:

| pH | Partition Coefficient = $ln(a_w/a_o)$ | |
|---|---|---|
| | Maximum | Preferred |
| 5 | 2 | <1.5 |
| 6 | 2 | <1.5 |
| 7 | 5 | <5 |
| 8 | 9 | <8 |

Compounds or complexing agents which are particularly suitable for producing technetium complexes with the desired partition coefficient and liver specificity characteristics have already been described in general terms and are typically exemplified by meta- and para-mercapto benzoic acid and their derivatives, the thioenol compound

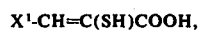

where $X^1$ is a lipophilic group (e.g. a furan moiety), and aliphatic mercaptans containing a water-solubilizing group, typically of the following structural formula:

  (I)

wherein
R³ and R⁴ are hydrogen or alkyl, preferably methyl,
n is an integer from 1 to 5, preferably 2 to 4 when R³ and R⁴ are hydrogen, and
X can be one of the following groups:
hydroxyl; primary, secondary, or tertiary amine, the secondary and tertiary amines being preferably substituted with lower aliphatic groups (the term "lower" is used to mean groups with less than 7 carbon atoms);
an alpha-amino acid moiety, provided that the radical $-\!\!+\!\!CR^3R^4\!\!+\!\!_n$ contains at least three carbon atoms in any branched or straight chain configuration and/or provided that the carboxylic acid or amine function of the alpha-amino acid moiety is blocked or substituted with an ionization-preventing radical, e.g. by acylation of the amine;
a carboxylic acid group, provided the $-\!\!+\!\!CR^3R^4\!\!+\!\!_n$ radical contains at least three carbon atoms;
an aliphatic chain (preferably containing less than 31 carbon atoms) terminated with a carboxylic acid group and optionally substituted with an additional mercapto (SH) group;
an N-aliphatic substituted hydrazine moiety, wherein the terminal $-NH_2$ is optionally converted to an amide;
an amido group, preferably acetamide or other lower aliphatic amide; and
phenolic groups, provided that the phenolic nucleus contains at least one additional water-solubilizing group (e.g. one of the previously described "X" groups) in addition to the phenolic hydroxyl.
Thus, in structural formula (I), examples of suitable X radicals include

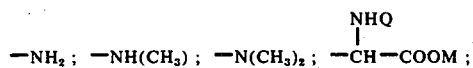

where
Q is a blocking group such as N-acetyl, and
M is hydrogen or a pharmaceutically acceptable cation;

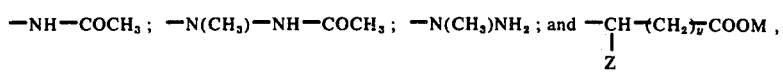

where
y is a positive integer less than 31, preferably less than 6,
M is as defined previously, and
Z is hydrogen or, preferably, a mercapto group.
As will be apparent from the foregoing examples, both ionizable (including protonatable) and nonionic X groups can be used, but groups capable of forming zwitterions or other stable internal salt groups are not preferred. Apparently, zwitterions may have a tendency to be removed by the kidney, while aliphatic amines, aliphatic alcohols, and carboxylic acids are less likely to have this tendency.
Typical preferred members of the previously described classes of compounds include: N-acetyl-penicillamine (which is greatly preferred to penicillamine itself, since the amine group is blocked), the omega:-mercaptoalkanols (2-mercaptoethanol, 3-mercaptopropanol, and 4-mercaptobutanol, 4-mercapto-2-methyl-2-butanol, p-mercaptobenzoic acid, 2-mercaptoethylamine, 6,8-dihydrothioctic acid, and alpha-thio-2-furan pyruvic acid.
The term "lipophilic" is not an absolute term, but like the terms "hydrophilic", "aqueous", "dispersion", etc., it has well understood meaning; see the "DEFINITIONS" in Columns 2 and 3 of U.S. Pat. No. 3,069,370 (Jansen et al), issued Dec. 18, 1962.
The term "substantially isotonic with mammalian body fluids", as used herein, denotes the situation obtained when the osmotic pressure exerted by the solution in question is sufficiently similar, as compared to a body fluid such as blood, so that no dangerous hypo- or hypertonic condition results in the patient or test animal when 0.1 ml (in the case of a mouse) or up to 10 ml (in the case of a human) of the solution is injected into the patient's or animal's bloodstream.
The exact mechanism by which the complexing agents used in this invention become chemically linked to technetium is difficult to determine. It appears that the Tc-99m should be present primarily in an oxidation state of at least about +3 but not more than +6. This oxidation state can be conveniently obtained by reducing 99m-pertechnetate, a relatively stable +7 technetium species. The reduced species can co-ordinate with one or two sulfur atoms which are in the form of mercaptan groups or the like. Complexing Tc with polymercaptans capable of chelating the Tc is preferred for stability; provided, at least one of the previously defined solubilizing ("X") groups is present. Non-solubilized chelates can be liver specific but are not necessarily excreted into the bile; therefore, they are better suited for liver structure studies than liver function studies.
The amount of Tc-99m needed to produce an amount of radiopharmaceutical suitable for most diagnostic or research uses is extremely small and is generally in the range of about 0.01 millicuries per milliliter (mc/ml) of 99m pertechnetate solution up to about 500 mc per ml of such solution. Only about $0.03 \times 10^{-10}$ gram of 99m-pertechnetate dissolved in a milliliter of aqueous medium (e.g. isotonic saline) is needed to provide 0.01 mc/ml, and less than $100 \times 10^{-10}$ gram of 99m-pertechnetate per milliliter of solution provides enough radioactivity for most uses. Due to the short half-life of the Tc:99m, it is preferred to prepare small batches of 99m-pertechnetate solution for immediate use. Batches as small as 0.1 ml can be adequate for animal studies (e.g. for injection in mice) and batches as large as 50 ml are convenient for one or more injections in one or a group of human patients. In any event, it would be a rare situation that required more than about $100 \times 10^{-10}$ gram (i.e. about $10^{-10}$ gram-atoms) of Tc99m as pertechnetate ion to produce a few ml of radiopharmaceutical, regardless of stoichiometry of the Tc complex. It is preferred to provide enough complexing agent (ordinarily at least $5 \times 10^{-9}$ moles per milliliter of reaction mixture) to have an excess over stoichiometry with respect to the Tc99m in the reaction mixture. A large excess of complexing agent (e.g. 0.5 – 1000 micromoles of complexing agent per ml of reaction mixture) can be desirable, particularly when the complexing agent itself serves as the means for reducing the oxidation state of pertechnetate.

Combinations of complexing agents or reducing agents can be used to achieve desired effects such as lower toxicity or greater chemical or biological stability.

The Tc-99m used in this invention is obtainable from a Mo-99 generator in the conventional manner. Eluting or "milking" the generator with an aqueous medium will provide the 99m-pertechnetate solution in the form of $M^{+x}(99mTcO_4^-)_x$, where $M^{+x}$ is a pharmaceutically acceptable cation such as a proton, an alkali metal ion, an ammonium ion, or the like, and $x$ is a positive integer less than four. Typically, the aqueous elution medium is a saline solution, which provides sodium 99m-pertechnetate.

The pertechnetate ion can be reduced chemically or electrolytically to a lower oxidation state of technetium, preferably by reaction with an oxidizable low valence metal salt such as a tin (II) salt (e.g. $SnCl_2$), an iron (II) salt (e.g. a ferrous salt/ascorbic acid medium), a Cu(I)/Cu(II) couple, a combination thereof, or other chemical reducing agents such as mercaptans, metal hydrides, thiosulfates, hypophosphites, bromides, iodides, etc. A particularly suitable means for providing the reducing agent and complexing agent is to pre-formulate a radiopharmaceutical kit for use with the Mo-99 generator. For example, 0.1 (preferably at least 0.5) to 10 ml. of a solution containing about 0.5 to about 1000 $\mu$ mole/ml of complexing agent and a suitable amount, e.g. 0.01 – 100 micromoles/ml of reducing agent can be hermetically and aseptically sealed in separate vials or the same vial. A preservative such as benzyl alcohol is optionally included in the contents of the vial. The solution in the vial is preferably substantially isotonic with mammalian body fluids, e.g. human blood. The contents of the vial can be combined with the pertechnetate-containing, substantially isotonic eluate, mild heat can be applied if necessary to the combined solutions to achieve the reduction and Tc-complex formation, and the resulting radio-pharmaceutical can then be injected into the blood stream of the patient or test animal. Radioactivity measurements are made in the conventional manner for a period from the time of injection until about 24 hours afterwards, depending on the nature of the study or diagnosis. Most studies call for at least one half hour of post injection radioactive measurements. These can be corrected for decay in the usual manner and studied with a view toward obtaining a picture of liver or gallbladder function. If the patient or test animal is placed on an appropriately controlled diet prior to liver uptake of the Tc-99m radiopharmaceutical, the bile, which will contain Tc-99m, will be introduced into the gut by the gallbladder, thus providing an opportunity for cholecystography. The gallbladder will not concentrate the Tc-99m if the patient has ingested fatty foods prior to and after the injection.

The amount of complexing agent injected into a test animal or human patient should preferably be less than 5% (e.g. less than 10%) of the LD 50 in mg per kg of body weight, though higher amounts are permissible in veterinary medicine. Typical LD 50's (determined in rodents and at least one other species) for preferred complexing agents of this invention range from about 0 to about 500 mg per kg of body weight.

As pointed out in the previous discussion regarding partition coefficients, a balance of lipophilic and hydrophilic properties is preferred for the Tc-complexing agents of this invention. Aliphatic mercapto alcohols, amines, and amides appear to provide this balance through the lipophilic contribution of the aliphatic portion of the molecule and the hydrophilic contribution of the amine or hydroxyl radical. (After complexing with Tc, the mercapto group is probably not sufficiently free to affect the solubility characteristics of the complex.) Aliphatic mercapto amines and amides can be derived from a hydrazine nucleus, so to speak, as in the case of N-methyl,N-(2-mercapto ethyl)-N'-aceto hydrazine and N-methyl,N-(2-mercapto ethyl)hydrazine.

An especially preferred class of complexing agents includes the mercapto-substituted aliphatic carboxylic acids and salts thereof. The mercapto group can be substituted on a primary, secondary, or tertiary carbon atom, as exemplified by 6,8-dihydrothioctic acid ($HS—C_2H_4—CH(SH)—C_4H_8COOH$) thiolactic acid, $HS—CH(CH_3)COOH$, and N-acetyl penicillamine. Alpha-amino acids (such as penicillamine) having sufficient aliphatic character are marginally operative as complexing agents in this invention, but it is preferred to block the alpha-amino group with, for example, an N-acetyl substituent. Thus, cysteine-Tc lacks sufficient liver specificity and is not useful in this invention.

When optical isomerism is possible, as in the case of dihydrothioctic acid, DL-racemic mixtures are fully operative in the invention and are easier to synthesize than the individual isomers. If desired, however, racemic mixtures can be resolved by conventional techniques.

A complexing agent of this invention preferably contains one of the aforementioned hydrophilic groups (amine, amide, alcohol, acid, ester, salt, etc.) but need not be water soluble. Dispersible, but substantially water insoluble, complexing agents can be dispersed in water by conventional techniques such as agitation. For example, higher hydrocarbon groups or chains in the complexing agent (e.g. 6- to 31-carbon saturated or unsaturated aliphatic chains, terminated with a carboxylic acid group or the like), though sharply reducing or preventing the water solubility of the complexing agent, would nevertheless permit the formation of stable aqueous suspensions or emulsions.

Acid, salt, hydroxyl, amino or other polar groups present on the complexing agent molecule can provide a water solubilizing or hydrophilic effect which is reflected in higher $ln\ a_w/a_o$ values, but due regard must be accorded to the variety of fluids, organs and tissues in mammals, each of which can have a distinctively acidic or basic environment, ranging from, for example, the low pH of the stomach to the relatively high pH of the intestines. The blood is on the mildly alkaline side at $pH = 7.4$. Thus, partition coefficient data on the Tc-complexes of this invention are preferably obtained throughout the pH range of 5 to 8. The use of partition coefficient data in pharmacology is well-established; see Andrejus Korolkvas, *Essentials of Molecular Pharmacology*, Wiley (interscience), N.Y., N.Y., 1970. It has now been found that the water/n-octanol system provides useful data for evaluating lipophilic-hydrophilic balance of Tc-complexes without in vivo testing. Natural logarithms of partition coefficients are tabulated in several of the Examples which follow.

Due regard should also be given to chelating effects of some water solubilizing groups such as COOH (or other acid groups) or OH. Thus, aromatic mercaptans preferably contain a solubilizing ("X") group meta or para to the SH group in addition to or in lieu of ortho- OH or ortho-COOH. A solubilizing group substituted on a second fused or independent aromatic ring serves the same purpose as the meta or para "X" group.

When the complexing agents of this invention are combined with a oxidizable low valence metal salt, the salt can be added to a water solution of the complexing agent. For example, dihydrothioctic acid can be dissolved in a sodium bicarbonate-water solution and a reducing agent comprising an excess over stoichiometry of $$SnCl_2.2H_2O$$

dissolved in ethanol can then be added to the solution. After the complexing and reducing agents have been combined, 99m sodium pertechnetate can be added. Agitation at a normal ambient temperature (20°–25° C.) will initiate the reduction step, and over 50% (in practice, more than 80%) of the pertechnetate ion will be in reduced form after less than an hour at this ambient temperature. The extent of reduction can be determined with thin layer chromatography (T.L.C.) and radiation monitoring, snce $TcO_4^-$ and its reduced-and-complexed form have distinctly different $R_f$ values if the chromatogram is developed with properly selected solvents.

If the oxidizable low valence metal salt is omitted, the sodium pertechnetate eluate can be reacted with HBr to form $H_2{}^{99m}TcBr_6$. This reaction is preferably carried out by repeatedly evaporating the eluate in the presents of >0.1N (up to concentrated) HBr or using a dry, inert gas such as nitrogen. The $H_2TcBr_6$ can be extracted with acetone, reacted with an excess of the mercaptan complexing agent in a non-aqueous medium to form the Tc-complex, and then worked up in saline solution or the like. Further pH changes can be used, if necessary to dissolve the Tc complex. The substantially isotonic radiopharmaceutical is then ready for injection.

The distinct $R_f$ values of novel Tc-mercaptan compounds or complexes produced according to this invention can reliably characterize these compounds so that they are distinguished from their precursors. Since only minute amounts of complexes of $Tc^{99m}$ an be produced, analysis of the complex by any method other than T.L.C. is extremely difficult at best. To reproducibly determine the $R_f$ values, thin layer chromatographs can be made from appropriate solutions and a standardized chromatogram sheet. Reproducible results have been obtained with unactivated 100 micron-thick silica gel chromatogram sheets having a polyvinyl alcohol binder and a neutral pH. One commercially available form of such a chromatogram is obtainable from Eastman Kodak Company as EASTMAN CHROMAGRAM Sheet 6060, described in the references noted in Kodak Publication Number JJ-7, available from Eastman Kodak Company.

Several thin layer chromatograms can be made and averaged as a double check on the experimental error inherent in the $R_f$, but generally this error is very small. The chromatograms are developed with polar solvent systems such as ethanol:water:ammonium hydroxide, as described subsequently.

The invention is illustrated by the non-limiting Examples which follow.

EXAMPLE 1

Tc - Dihydrothioctic Acid, Preparation and Distribution in Mice

One microliter of DL-6,8-dihydrothioctic acid (hereinafter referred to an DHT)*was placed in an an evacuated $N_2$ flushed pharmaceutical vial. One ml of water and 1.3 molar-equivalents $NaHCO_3$ (based on eq. of COOH) were added and the sample shaken vigorously to dissolve the DHT. Twenty-five microliters of absolute ethyl alcohol containing enough $SnCl_2.2H_2O$ to provide 10 micrograms of Sn (II) were added. Four ml of $Na^{+99m}TcO_4^-$ (0.93 millicurie 99m Tc) were added, the vial vigorously shaken, then allowed to stand for 16 minutes at normal ambient temperature. Analysis with thin layer chromatography (T.L.C.) using anhydrous acetone and an EASTMAN CHROMAGRAM 6060 (described subsequently) showed 0.3% unreacted 99m - pertechnetate.

*DHT is disclosed in Wagner et al, *J. Amer. Chem. Soc.* 33, 5079 (1956).

The solution was diluted to 4 microcuries of 99m Tc per ml and 0.1 ml of this solution was injected, i.v. (intravenously) in the tail vein of each of seven female Swiss Webster white mice. The mice were sacrificed at the following time periods: 0, ½ hr., 2½ hr., 4 hr., 6 hr., and 24 hrs. The organs of each mouse were isolated and the distribution of 99m Tc determined by assay with a Packard series 410A Auto-Gamma Spectrometer.

The results of this study are shown in Table IA.

TABLE IA

Distribution of 99mTc from Dihydrothioctic Acid - 99mTc Mercaptide in Mice as a Function of Time...

| Organ | Percent of Total Injected 99mTc as a Function of Time* | | | | | | |
|---|---|---|---|---|---|---|---|
| | 0 | 0.5 hr. | 1 hr. | 2.5 hrs. | 4 hrs. | 6 hrs. | 24 hrs. |
| Lungs | 3.58 | 0.65 | 0.41 | 0.16 | 0.04 | 0.05 | 0.06 |
| Liver | 32.2 | 27.5 | 19.8 | 5.46 | 5.25 | 2.66 | 1.36 |
| Spleen | 0.10 | 0.12 | 0.06 | 0.00 | 0.01 | 0.02 | 0.07 |
| Kidneys | 5.47 | 2.49 | 1.02 | 0.74 | 0.38 | 0.52 | 0.12 |
| Stomach | 0.78 | 0.22 | 0.13 | 0.12 | 0.33 | 0.07 | 0.00 |
| Intestines | 7.23 | 16.24 | 26.49 | 23.77 | 6.89 | 3.90 | 0.34 |
| Bladder | 0.03 | 0.11 | 0.04 | 0.01 | 0.00 | 0.00 | 0.08 |
| Pancreas | 0.49 | 0.07 | 0.04 | 0.03 | 0.01 | 0.00 | 0.00 |
| Carcass | 28.0 | 10.3 | 7.01 | 1.19 | 1.42 | 1.37 | 1.08 |

*Activity corrected for radioactive decay and counting efficiency for each organ. Subsequent studies showed that the percentages in Table IA, in absolute terms, are subject to a large experimental error, but nevertheless are very useful as relative values.

The experimental error in the distribution vs. time data for the 99mTc-DHT complex was minimized by averaging six runs under identical conditions, always with the female Swiss Webster mice. The effect of organ geometry on radioactivitty counting efficiency was taken into account. Corrections were radioactivity made so that, upon extrapolation back to time zero, the summation of activity in the organs was equal to the injected activity (i.e. by comparison to 0.1 ml standards). Intestines were assayed as two samples and the carcass as four samples due to the relatively large volumes of these samples.

The preparation of the 99mTc-DHT complex was optimized by following the previously outlined procedure but with the following amounts of the reactants:

| | |
|---|---|
| DHT | 2.3 mg |
| Stannous ion | 20 micrograms |
| NaHCO$_3$ | 0.06 millimoles |
| 99mTcO$_4^-$ solution | 4.5 ml, containing 1.0 mc 99mTc. |

The reaction was run at ambient temperature for 15 minutes prior to dilution of the reaction medium to 4 microcuries/ml for injection into the mice. The results are reported in Table I-B.

TABLE IB

Further 99mTc-DHT Studies in Mice
Percentage of Total Injected 99mTc as a Function of Time**

| Organ | 5 min. | 0.5 hr. | 1 hr. | 2 hr. | 4 hr. | 6 hr. | 24 hr. |
|---|---|---|---|---|---|---|---|
| Lungs | 1.33 | 0.70 | 0.49 | 0.27 | 0.06 | 0.04 | 0.01 |
| | ±0.69 | ±0.14 | ±0.14 | ±0.20 | ±0.06 | ±0.04 | ±0.04 |
| Liver | 62.9 | 45.4 | 27.4 | 11.8 | 6.26 | 4.46 | 1.64 |
| | ±5.7 | ±10.9 | ±6.0 | ±4.0 | ±1.09 | ±1.16 | ±0.57 |
| Spleen | 0.14 | 0.09 | 0.04 | 0.03 | 0.01 | 0.01 | 0.09 |
| | ±0.06 | ±0.04 | ±0.01 | ±0.03 | ±0.01 | ±0.01 | ±0.17 |
| Kidneys | 5.37 | 2.76 | 2.23 | 1.53 | 0.89 | 0.80 | 0.37 |
| | ±1.37 | ±0.24 | ±0.63 | ±1.01 | ±0.29 | ±0.24 | ±0.41 |
| Stomach | 0.41 | 0.40 | 0.34 | 0.70 | 0.34 | 0.63 | 0.06 |
| | ±0.47 | ±0.14 | ±0.39 | ±0.73 | ±0.20 | ±0.43 | ±0.09 |
| Intestines | 7.37 | 29.4 | 35.7 | 43.9 | 28.9 | 19.3 | 0.83 |
| | ±0.71 | ±4.0 | ±4.8 | ±7.6 | ±14.6 | ±16.9 | ±0.31 |
| Carcass | 21.0 | 9.83 | 6.83 | 4.39 | 1.47 | 1.33 | 1.19 |
| | ±7.9 | ±1.89 | ±1.44 | ±4.74 | ±0.83 | ±1.09 | ±1.57 |
| Urine and Feces* | 1.49 | 11.3 | 26.9 | 37.4 | 62.1 | 73.4 | 95.8 |

*By difference
**Average of 6 studies

These studies clearly show the removal of the 99mTc complex from the blood by the liver and its excretion into the intestine and finally out in the feces.

T.L.C. analysis of the Tc-dihydrothioctic acid (Tc-DHT) complex was carried out as follows:
Chromatogram:
Unactivated 100-micron thick silica gel sheet with polyvinyl alcohol binder, neutral pH (EASTMAN CHROMAGRAM 6060)
Solvent systems:
1. anhydrous acetone
2. ethanol:water:concentrated ammonium hydroxide in the volume/volume/volume ratio of 95:17:16
Developed chromatograms:
When developed with solvent (1), $R_f = 0$ for the Tc-DHT complex, but the $R_f$ was about 1.0 for unreacted pertechnetate;
When developed with solvent (2), $R_f = 0.66$ for the Tc-DHT complex; $R_f = 0.75$ for unreacted pertechnetate.
Partition coefficients for the Tc-DHT complex of this Example were determined with a water/n-octyl alcohol system over the pH range of 5 to 8 using radioactive measurements to determine the amount of Tc-99m in each phase. The expression $a_w/a_o$ is the ratio of the activity in water to the activity in n-octyl alcohol. For comparison, partition coefficients over the same pH range were determined for sodium 99m pertechnetate and cysteine (HS-CH$_2$CH(NH$_2$)COOH). The results are reported in Table II.

TABLE II

Ln of Partition Coefficients vs. pH

| pH | 99mTc-DHT* Complex, ln($a_w/a_o$) | Na99mTcO$_4$ ln($a_w/a_o$) | 99mTc-Cysteine, ln($a_w/a_o$) |
|---|---|---|---|
| 5.0 | −1.8 | +3.2 | +3.7 |
| 6.0 | +1.2 | +3.3 | +3.9 |
| 7.0 | +4.3 | +3.5 | +4.1 |
| 8.0 | +7.4 | +3.6 | +4.3 |

*DHT = D,L-6,8-dihydrothioctic acid

The natural logarithms in the above Table are accurate to ± 0.5. The $ln(a_w/a_o)$ curve for the Tc-DHT complex reflects a marked dependence of partition coefficient upon pH. Although this invention is not bound by any theory, it is believed that the free acid (—COOH) form of the DHT-Tc complex is lipophilic and soluble in cell membranes, while the carboxylic acid salt form is soluble both in blood and non-biological aqueous media. It is further theorized that the observed in vivo performance of the DHT-Tc complex is due in part to the solubility of the free acid form in cell membranes and the apparent ability of this species to pass easily from the blood to the bile. Fortunately, this capability does not appear to detract from the compatibility of the salt form with aqueous media.

Technetium complexes or species with partition coefficient data outside the "maximum" range described previously (e.g. pertechnetate ion and 99mTc-cysteine) have also been studied in vivo and found to have insufficient liver or gall-bladder specificity to be useful in the preferred type of organ function studies contemplated by this invention.

EXAMPLE 2

Gamma Ray Monitoring in Anesthetized Dog

To a pharmaceutical vial containing 1.0 microliter of DL-6,8-dihydrothioctic acid was added 1.0 ml 0.0067 normal NaHCO$_3$. The sample was vigorously shaken to dissolve the dihydrothioctic acid. Twenty-five microliters of absolute ethyl alcohol containing 10 micrograms Sn (II) as SnCl$_2$.2H$_2$O was added. Then 2.31 millicuries Na 99mTcO$_4^-$ eluate in 4 ml saline was added. After 15 minutes at room temperature, a thin layer chromatogram was run with anhydrous acetone according to the method outlined in Example 1, and 2.1% unreacted 99m-pertechnetate was found.

Liver imaging, analysis of liver function, and cholecystography were carried out by intravenous injection of 412 microcuries in 1.0 ml of this solution into an anesthetized, fasted dog positioned with its liver under a gamma camera. The output of the gamma camera was attached to a computer so the data could later be played back, displayed, photographed and analyzed. At a period of 20 minutes post-injection, the liver was clearly visualized. As time passed, the 99mTc could be seen to concentrate in the gallbladder region until at 150 minutes post-injection, the ratio of activity per 100 cells over the gallbladder region was 12.6 times that over the liver. After 180 minutes, a gallbladder stimulus comprising 2 dog units/Kg of cholecystokinin was administered. Within 20 minutes the activity/100 cells over the gallbladder region had dropped to 33 percent of its value at 150 minutes.

EXAMPLE 3

Part A - Preparation of 4-Mercapto Butanol
4-mercapto butanol was prepared as follows:

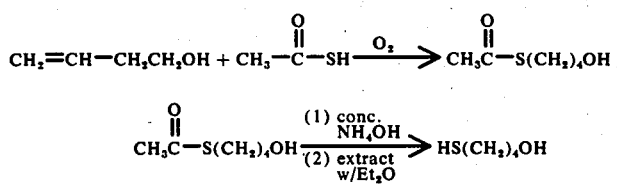

4.110 gm. $CH_2 = _{CHCH2}CH_2OH$*plus 4.772 gm.

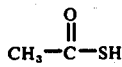

were sealed in a 20 ml pharmaceutical vial which was then evacuated, flushed with oxygen and vigorously shaken. After approximately 2 minutes, the vial became spontaneously hot. After the vial cooled, it was analyzed, by G.L.C. (gas-liquid chromatography) and found to have

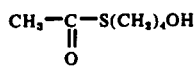

present in 87.7% purity.
*Commercially available from Aldrich Chemical Co., Inc.

Twenty ml conc. $NH_4OH$ was added and the sample was vigorously shaken. The $HS(CH_2)_4OH$ was extracted with diethyl ether ($Et_2O$) which was dried over $CaSO_4$ and the ether evaporated in vacuo. The 4.779 gm. of isolated product was found to be 87.4% pure 4-mercaptobutanol by G.L.C.

In a second run, the S-acetyl-4-mercaptobutanol was prepared in 98.0% purity (100% recovery) and hydrolyzed to yield 4-mercaptobutanol in 97.9% purity.

Part B - 4-Mercaptobutanol-99m Tc Mercaptide

One ml of $Na^+$ 99m $Tc_4^-$ was evaporated three times with 1 ml 48% HBr under a stream of nitrogen on a steam bath. The $H_2^{99m}TcBr_6$ was extracted with 3 ml acetone. To 0.7 ml of this solution there was added 1 ml 0.03M $HS(CH_2)_4OH$ in acetone. After 10 minutes at room temperature, 1 ml saline was added and the acetone removed on a steam bath under a stream of nitrogen. An additional 1 ml of saline was added and the solution further diluted with saline to 4 microcurie 99m-Tc/ml. One-tenth ml of this solution was injected in each of six female Swiss Webster white mice, each mouse weighing approximately 20 g. The mice were sacrificed at periods of 0.25, 0.5, 1.0, 2.0, 4.0, and 24.0 hours. The organs were isolated and the distribution of 99m Tc determined. To a large extent, the agent was rapidly removed from the blood by the liver and excreted in the bile into the intestines and ultimately out in the feces.

The T.L.C. (thin layer chromatography) analysis of the 99m-Tc-4-mercaptobutanol complex was carried out with unactivated, 100-micron thick, silica gel/polyvinyl alcohol, neutral pH chromatograms (EASTMAN CHROMAGRAM 6060) as in Example 1. The solvent systems were: anhydrous acetone and anhydrous methanol. Results were:

anhy. acetone, $R_f = 0$ (compared to about 1.0 for pertechnetate)

anhy. methanol $R_f = 0.69$ (compared to 0.73 for pertechnetate)

The $a_w/a_o$ ratios for the 99mTc-4-mercaptobutanol complex were determined as in Example 1, except that two independently determined $\ln(a_w/a_o)$ vs. pH plots were averaged. The results are given in the following Table.

TABLE III

| pH | Ln of Partition Coefficients vs. pH ln ($a_w/a_o$) [average of 2 runs] |
|---|---|
| 5.0 | −1.1 |
| 6.0 | −0.9 |
| 7.0 | −0.8 |
| 8.0 | −0.7 |

These data indicate good lipophilicity and adequate compatibility with aqueous media throughout the pH range.

EXAMPLE 4

4-Mercaptobutanol-99mTc Complex Distribution in Mice

One ml of 3N HCl, 0.5 ml ethyl alcohol, 90 mg. benzyl alcohol and 45 mg $HS(CH_2)_4OH$ were placed in a 20 ml pharmaceutical vial which was sealed and put under an atmosphere of $N_2$. One ml of 99m $TcO_4^-$ eluate and 6.5 ml saline were added. The sample was heated 10 minutes on the steam bath, then cooled to room temperature and 3.5 ml of (86.6 mg/ml) sodium acetate in water were added. The sample was diluted to 4 microcuries/ml and 0.1 ml of this solution was injected i.v. (intravenous) in each of seven (approximately 20 gm) female Swiss Webster white mice. At appropriate time periods the mice were sacrificed, their organs isolated and assayed for 99m Tc activity in a gamma spectrometer. The values were corrected for radioactive decay, and counting efficiency compared to 0.1 ml standards of the solution. This data, shown in Table II, clearly shows the concentration of 99m Tc in the liver followed by its excretion into the intestines and out in the feces and constitutes a useful liver function test.

TABLE IV

Distribution of 99m Tc from $HS(CH_2)_4OH$ - 99m Tc Mercaptide in Mice as a Function of Time
Percent of Total Injected 99m Tc as a Function of Time*

| Organ | 0 | 0.5 hr. | 1 hr. | 2 hr. | 4 hr. | 6 hr. | 24 hr. |
|---|---|---|---|---|---|---|---|
| Lungs | 4.46 | 1.07 | 0.86 | 0.61 | 0.41 | 0.36 | 0.41 |
| Liver | 30.20 | 23.03 | 18.40 | 16.06 | 11.84 | 12.19 | 10.78 |
| Spleen | 0.19 | 0.18 | 0.14 | 0.15 | 0.10 | 0.11 | 0.00 |
| Kidneys | 7.38 | 2.51 | 1.96 | 1.68 | 1.18 | 1.03 | 0.61 |
| Stomach | 0.85 | 0.86 | 1.10 | 0.54 | 0.86 | 0.34 | 1.66 |
| Intestines | 10.42 | 37.90 | 31.41 | 18.41 | 10.93 | 2.36 | 10.32 |
| Bladder | 0.05 | 0.04 | 0.03 | 0.02 | 0.02 | 0.00 | 0.01 |
| Pancreas | 0.77 | 0.25 | 0.12 | 0.23 | 0.10 | 0.10 | 0.00 |
| Carcass | 42.35 | 14.22 | 10.80 | 11.56 | 7.86 | 6.70 | 6.74 |

*See Note to Table I in Example 1

EXAMPLE 5

α-Thio-2-Furan Pyruvic Acid - 99m Tc Complex

As in previous Example, 3, 1 millicurie 99m $TcO_4^-$ in 1 ml eluate from a generator was evaporated to dryness under a stream of $N_2$ three times with 1 ml of 48% HBr. The $H_2TcBr_6$ residue was extracted with 3 ml of dry acetone. One ml of this solution was added to 1 ml of 0.03 molar alpha-thio-2-furan pyruvic acid* in acetone. After ten minutes, one ml of saline was added, and the acetone was evaporated under a stream of $N_2$. One ml of saline was added plus one drop 2N NaOH to yield pH of 9. The solution was injected i.v. in the tail vein of six, approximately 20 gram, female Swiss Webster mice. The mice were sacrificed at appropriate periods of time. The organs were isolated and the activity distribution determined. This distribution, shown in Table V, clearly shows the removal of the technetium complex from the blood by the liver, followed by excretion of the technetium complex in the bile into the intestines and ultimately excretion in the feces. This constitutes a liver function test, the kinetics which can be followed in a human patient for example, by using a gamma camera or a rectilinear scanner.

*Commercially available from Aldrich Chemical Co., Inc.

TABLE V

Distribution of 99m Tc from alpha-thio-2-furan Pyruvic Acid 99m Tc Mercaptide in Mice as a Function of Time
Percent of Total 99m Tc in Mice as a Function of Time*

| Organ | 0.25 hr. | 0.5 hr. | 1 hr. | 2 hr. | 4 hr. | 24 hr.** |
|---|---|---|---|---|---|---|
| Lungs | 3.25 | 1.85 | 0.76 | 0.97 | 0.38 | 0.26 |
| Liver | 48.7 | 42.4 | 34.3 | 31.7 | 23.9 | 9.31 |
| Kidneys | 4.04 | 4.34 | 3.49 | 3.85 | 3.13 | 3.58 |
| Stomach | 6.64 | 8.42 | 5.89 | 7.69 | 2.04 | 0.00 |
| Intestines | 10.8 | 16.3 | 26.5 | 35.9 | 63.1 | 1.69 |
| Pancreas | 0.84 | 0.40 | 0.26 | 0.34 | 0.09 | 1.00 |
| Carcass | 25.81 | 26.2 | 28.7 | 19.8 | 7.16 | 4.33 |

*These values are not corrected to 0.1 ml standards as in previous examples, and the footnote to Table as applicable here also.
**Included urine and feces in total.

The $a_w/a_o$ ratios for the Tc 99m complex of this Example were determined as in Example 1. The results (ln data accurate to ± 0.5) were as follows:

TABLE VI

Ln of Partition Coefficients vs. pH

| pH | $\ln(a_w/a_o)$ |
|---|---|
| 5.0 | +1.0 |
| 6.0 | +1.1 |
| 7.0 | +1.3 |
| 8.0 | +1.5 |

EXAMPLE 6

Partition Coefficients of 99mTc-Aliphatic Mercapto Alcohol Complexes

A series of Tc-99m complexes were made by reducing $NaTcO_4$ and reacting the reduced Tc-99m species with the following aliphatic mercapto alcohols:
  2-mercapto ethanol
  3-mercapto propanol
  5-mercapto pentanol [omega-mercapto-n-amyl alcohol]
  4-mercapto-2-methyl-2-butanol
(For the data on the 4-mercaptobutanol complex, see Table III of Example 3(B).)

The natural logarithms of the partition coefficients at various pH levels for the water/n-octanol system are set forth in the following table. Partition coefficients were determined as in Examples 1, 3, and 5 in Tables II, III, and VI.

TABLE VII

Partition Coefficients of Tc-99m Complexes

| Complexing Agent | ln $a_w/a_o$ At Various pH Levels | | | |
|---|---|---|---|---|
| | pH=5 | pH=6 | pH=7 | pH=8 |
| 2-mercapto-ethanol | −0.9 | −0.8 | −0.7 | −0.6 |
| 3-mercapto propanol | −0.5* | −0.4* | −0.3* | −0.2* |
| 5-mercapto pentanol | −0.2 | −0.1 | −0.1 | 0.0 |
| 4-mercapto-2-methyl-2-butanol | +1.0 | +1.1 | +1.2 | +1.3 |

*Average of two runs

Partition coefficients in the above table have the same level of accuracy as those of Tables II and VI.

The $C_3$ and higher mercapto aliphatic alcohols were prepared from the appropriate unsaturated alcohols by the method of Example 3(A), i.e. by formation and cleavage of the S-acetyl group and extraction of the product with ether. Thus, 3-mercaptopropanol was prepared from allyl alcohol, 5-mercaptopentanol from 4-penten-1-ol, and 4-mercapto-2-methyl-2-butanol from 2-methyl-3-buten-2-ol.

EXAMPLE 7

99mTc-Para-Mercapto-Benzoic Acid 99mTc-2-Mercapto-Ethylamine

A. The compound para-aminobenzoic acid was substituted for ortho-aminobenzoic acid in the method outlined in Org. Syn. Collection, Vol. II, page 580. (Para-aminobenzoic acid is commercially available.) The 99mTc-p-mercaptobenzoic acid complex was prepared using sodium 99m pertechnetate and HBr, as in Example 3(B). The complex was assayed by intravenous injection into the tail vein of Swiss Webster mice, as in Examples 1 and 4, the animals being sacrificed at 0.25, 0.5, 1, 2, 4, and 24 hours. The assay indicated rapid uptake by the liver and rapid excretion by the liver into the gut. Uptake by the lungs, kidneys, and stomach did not detract significantly from liver specificity.

B. The 99mTc complex of the compound 2-mercaptoethylamine was prepared from reduced sodium 99m pertechnetate. Using the Swiss Webster mice assay, outlined previously, this complex was found to be liver specific and rapidly excreted by the liver into the gut.

What is claimed is:

1. A stable radiopharmaceutical composition for preparing a biologically sterile liquid aqueous medium containing a liver specific agent labeled with technetium-99m comprising a compound for imparting liver specificity to technetium-99m selected from the group consisting of:
   N-acetyl penicillamine,
   2-mercaptoethylamine,
   2-mercaptoethanol,
   3-mercaptopropanol,
   4-mercaptobutanol,
   4-mercapto-2-methyl-2-butanol,
   2-mercaptoethylamine,
   6,8-dihydrothioctic acid,
   alpha-thio-2-furan pyruvic acid,
   p-mercaptobenzoic acid, and mixtures thereof;
and a pharmaceutically-acceptable reducing agent for pertechnetate, said compound being present in an amount sufficient to provide a concentration of about 0.5 to about 1000 micromoles per milliliter in said aqueous medium; and said reducing agent being present in an amount sufficient to provide a concentration of about 0.01 to about 100 micromoles per milliliter in said aqueous medium.

2. A composition according to claim 2 wherein said reducing agent comprises an oxidizable metal salt selected from the group consisting of a tin (II) salt, an iron (II) salt, a copper (I)/copper (II) couple, and mixtures thereof.

* * * * *